United States Patent [19]

Frankel et al.

[11] Patent Number: 4,683,086
[45] Date of Patent: Jul. 28, 1987

[54] AZIDO DERIVATIVES OF PENTAERYTHRITOL

[75] Inventors: Milton B. Frankel, Tarzana; Edgar R. Wilson, Simi Valley, both of Calif.

[73] Assignee: Rockwell International Corporation, El Segundo, Calif.

[21] Appl. No.: 766,460

[22] Filed: Aug. 19, 1985

[51] Int. Cl.$^4$ ............................................. C07C 117/00
[52] U.S. Cl. ..................................... 260/349; 549/510
[58] Field of Search .......................... 260/349; 549/510

[56] References Cited

U.S. PATENT DOCUMENTS

| | | | |
|---|---|---|---|
| 3,112,280 | 11/1963 | Farthing | 549/510 X |
| 3,301,923 | 1/1967 | Skovronek | 549/510 X |
| 4,432,814 | 2/1984 | Witucki et al. | 149/19.1 |
| 4,450,110 | 5/1984 | Simmons et al. | 260/349 |
| 4,522,756 | 6/1985 | Schack et al. | 260/349 |

OTHER PUBLICATIONS

Anderson, et al.; C. A., 97: 144284w (1982).
Rodd; Chemistry of Carbon Compounds, (1957), vol. IV, Part A, p. 5; Elsenier Pub. Co., N.Y.
Boyer, et al.; Chemical Reviews, 54, (1954), p. 2.
Noller; Chemistry of Organic Compounds, (1965), 3rd ed, pp. 145, 146, 292, W. B. Saunders Co., Phila.

*Primary Examiner*—Joseph Paul Brust
*Attorney, Agent, or Firm*—H. Fredrick Hamann; Harry B. Field; David C. Faulkner

[57] ABSTRACT

Diazido derivatives of pentaerythritol are prepared by reacting 3,3-bis(azidomethyl) oxetane with inorganic acids such as hydrobromic or nitric acid. The resulting diazido monobromide can be reacted with sodium azide to produce pentaerythritol triazide which can be subsequently nitrated to pentaerythritol triazido mononitrate. The pentaerythritol diazido mononitrate produced by the reaction of nitric acid with the above oxetane can be further nitrated with nitric acid to produce pentaerythritol diazido dinitrate. These diazido and triazido derivatives of pentaerythritol can be utilized as energetic azido plasticizers per se or can serve as intermediates for the production of such plasticizers.

9 Claims, No Drawings

AZIDO DERIVATIVES OF PENTAERYTHRITOL

BACKGROUND OF THE INVENTION

1. Field of the Invention

This invention relates to production of azido derivatives of pentaerythritol, and is particularly directed to the preparation of diazido and triazido derivatives of pentaerythritol, and to the process for producing same.

2. Description of the Prior Art

Solid propellants are formulated from an oxidizer and fuel together with suitable binders and plasticizers to impart physical integrity. Most highly energetic systems utilize binders and plasticizers containing energetic groups such as nitro (—$NO_2$), fluorodinitro (FC($NO_2$)$_2$—), difluoroamino (—$NF_2$), and many others.

Utilization of azido plasticizers has become a reality during the last several years. These azido plasticizers impart additional energy to propellants since each azido group present adds approximately 85 kcal/mole of energy to the system.

In U.S. application Ser. No. 766,459, filed Aug. 19, 1985, titled Polyazido Esters, by the same inventors as the present application and assigned to the same assignee as the present application, there is disclosed and claimed polyazido esters prepared from diazido and triazido derivatives of pentaerythritol. These derivatives include pentaerythritol triazide and pentaerythritol diazido mononitrate.

Heretofore, it has been attempted to prepare diazido and triazido derivatives of pentaerythritol based on the conversion of pentaerythritol to the dichloro and trichloro derivatives, followed by subsequent reaction with sodium azide to give pentaerythritol diazide and pentaerythritol triazide. However, this method for the preparation of the latter two compounds resulted in mixtures of mono, di, tri and tetra-substituted products. Consequently, the synthesis of the respective azido derivatives of pentaerythritol by such process was unsatisfactory.

SUMMARY OF THE INVENTION

The present invention accordingly provides a process for preparing diazido derivatives of pentaerythritol cleanly and in high yield by reacting 3,3-bis-(azidomethyl) oxetane with inorganic acids such as hydrobromic or nitric acid, in an appropriate solvent.

The resulting pentaerythritol diazido monobromide can be converted by treatment with sodium azide to produce pentaerythritol triazide which can be subsequently nitrated to pentaerythritol triazido mononitrate.

The pentaerythritol diazido mononitrate which can be produced by reaction of nitric acid with the above oxetane can be further nitrated with nitric acid to produce pentaerythritol diazido dinitrate.

The above diazido and triazido derivatives of pentaerythritol can be utilized as energetic plasticizers or can serve as intermediates for production of energetic azido plasticizers, in the production of solid propellants, gun propellants and explosives.

OBJECTS OF THE INVENTION

It is accordingly one object of the invention to provide an improved process for producing azido derivatives of pentaerythritol, particularly the diazido and triazido derivatives thereof.

Another object of the present invention is the production of diazido and triazido derivatives of pentaerythritol in substantially pure form.

A particular object of the invention is the production of diazido and triazido derivatives of pentaerythritol, particularly pentaerythritol diazido mononitrate and pentaerythritol triazide, cleanly and in high yield.

DESCRIPTION OF THE PREFERRED EMBODIMENTS

The reaction between 3,3-bis(azidomethyl) oxetane and an inorganic acid for producing diazido derivatives of pentaerythritol is as follows:

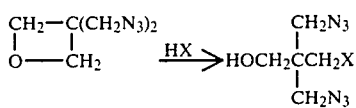

wherein HX is an inorganic acid, e.g. HBr or $HNO_3$, and X is a halogen, selected from the group consisting of Br, Cl, or I, or $ONO_2$.

The above reaction is carried out usually employing an excess of the inorganic acid, e.g. HBr or $HNO_3$ in a halogenated solvent, particularly a chlorinated solvent such as methylene chloride, carbon tetrachloride, chloroform or ethylenedichloride, preferably methylene chloride. The reaction can be carried out at temperature ranging from ambient temperature of about 20° C. to reflux temperatures.

After completion of the reaction the organic layer is separated, washed with water and dilute sodium bicarbonate solution, dried, e.g. over anhydrous sodium sulfate, and concentrated to give the final pentaerythritol diazido derivative, e.g. monobromide or mononitrate, in the form of an oil.

Pentaerythritol diazido monobromide can be reacted with sodium azide to produce pentaerythritol triazide, and the latter can be subsequently nitrated with nitric acid to produce pentaerythritol triazido mononitrate, as noted below:

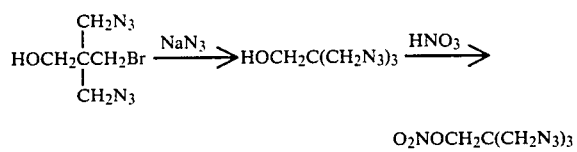

$O_2NOCH_2C(CH_2N_3)_3$

The reaction of the monobromide and sodium azide is carried out employing an excess of the azide, in an appropriate solvent such as dimethylsulfoxide, and at elevated temperature, e.g. 85°–90° C. The reaction mixture is diluted with water and a halogenated solvent such as methylene chloride is added. The organic phase containing the reaction product, pentaerythritol triazide, is separated and is dried, e.g. over anhydrous sodium sulfate, purified as by passage through a silica gel column and concentrated to give an oil as product.

The reaction of pentaerythritol triazide with nitric acid to produce the triazido mononitrate is carried out in a manner similar to the reaction of the oxetane and nitric acid, noted above, that is utilizing an excess of nitric acid in a halogenated solvent such as methylene chloride. The resulting organic layer is separated, washed, purified and concentrated as noted above to produce an oil product.

Pentaerythritol diazido mononitrate can be further nitrated with nitric acid to produce pentaerythritol diazido dinitrate as noted below:

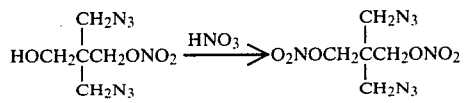

The above nitration is carried out in a manner similar to the reaction of the above oxetane with nitric acid.

The azido derivatives of pentaerythritol produced by the invention process accordingly have the general structural formula:

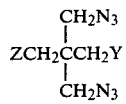

wherein Y is halogen, selected from the group consisting of Br, Cl or I, $ONO_2$ or $N_3$, and Z is OH or $ONO_2$.

The following are examples of practice of the invention, it being understood that such examples are only illustrative and not limitative of the invention.

EXAMPLE I

Pentaerythritol Diazido Monobromide

To a mixture of 258 g (1.5 mol) of 47% hydrobromic acid and 150 ml of methylene chloride was added dropwise 168 g (1.0 mol) of 3,3-bis(azidomethyl) oxetane in 30 min. The reaction temperature rose from 24° to 38° C. After the addition was complete, the reaction mixture was refluxed for two hours. The organic layer was separated, washed with water, dilute sodium bicarbonate solution, dried over anhydrous sodium sulfate, and concentrated to give 240.0 g (96.5%) of yellow oil, $n^{24}D$ 1.5436. The infrared spectrum was consistent for the expected structure with strong absorptions at $3.0\mu$ (hydroxyl) and $4.8\mu$ (azido).

EXAMPLE II

Pentaerythritol Diazido Mononitrate

To a solution of 16.8 g (0.1 mol) of 3,3-bis (azidomethyl) oxetane in 20 ml of methylene chloride was added 18.0 g (0.2 mol) of 70% nitric acid dropwise in 30 min. The temperature rose from 22° to 30° C. during the addition. The reaction mixture was stirred at ambient temperature for 69 hours, at which time G.C. analysis showed that all of the starting material had disappeared. The reaction mixture was washed with 50 ml water, 50 ml of dilute sodium bicarbonate, and 50 ml of water, dried over magnesium sulfate, and concentrated to give 17.9 g (77.5%) of yellow oil, $n^{25}D$ 1.5186. The infrared spectrum was consistent for the expected structure with strong absorptions at $3.0\mu$ (hydroxyl), $4.8\mu$ (azido) and $6.15\mu$ (nitrate).

EXAMPLE III

Pentaerythritol Triazide

A mixture of 189.4 g (0.76 mol) of pentaerythritol diazido monobromide, 98.9 g (1.52 mol) of sodium azide, and 570 ml of dimethylsulfoxide was heated, with good stirring, at 85°–90° C. for 48 hours. The reaction mixture was cooled to ambient temperature and diluted with 500 ml of water and 300 ml of methylene chloride. The organic phase was separated and washed with 10×1 liter of water to remove the inorganic salts and the dimethylsulfoxide. The methylene chloride solution was dried over anhydrous sodium sulfate, passed through a silica gel column, and concentrated to give 129.6 g (77%) of colorless oil, $n^{22}D$ 1 5319. The infrared spectrum was consistent for the expected structure with strong absorptions at $3.0\mu$ (hydroxyl) and $4.8\mu$ (azido).

EXAMPLE IV

Pentaerythritol Triazido Mononitrate

To a solution of 0.8 g (0.0078 mol) of acetic anhydride in 4 ml of methylene chloride was added 0.34 g (0.0052 mol) of 98% nitric acid at 0°–5° C. A solution of 1.0 g (0.0047 mol) of pentaerythritol triazide in 5 ml of methylene chloride was added dropwise in 10 min., keeping the temperature at 0.5° C. After addition was complete, the reaction mixture was allowed to warm to ambient temperature, stirred for an additional 30 min., and diluted with 10 ml of ice-water. The organic layer was separated, washed with dilute sodium bicarbonate solution and water. The methylene chloride solution was dried over anhydrous sodium sulfate, passed through a neutral column, and concentrated to give 1.07 g (89.2%) of colorless oil, $n^{22.5}D$ 1.5245. The infrared spectrum was consistent for the expected structure with strong absorptions at $4.8\mu$ (azido) and $6.15\mu$ (nitrate).

EXAMPLE V

Pentaerythritol Diazido Dinitrate

To a solution of 0.73 g (0.0072 mol) of acetic anhydride in 4 ml of methylene chloride was added 0.31 g (0.21 mol) of 98% nitric acid at 0°–5° C. A solution of 1.0 g (0.0043 mol) of pentaerythritol diazido mononitrate in 2 ml of methylene chloride was added dropwise in 10 min., keeping the temperature at 0°–5° C. The reaction mixture was stirred for an additional 5 min. at 0°–5° C. and then allowed to warm to ambient temperature. The reaction mixture was diluted with 10 ml of ice-water, the organic phase was separated, washed with dilute sodium bicarbonate solution and water. The methylene chloride solution was dried over magnesium sulfate, passed through a column of neutral alumina, and concentrated to yield 1.0 g (84%) of almost colorless oil, $n^{22.5}D$ 1 5161. The infrared spectrum was consistent for the expected structure with strong absorptions at $4.8\mu$ (azido) and $6.15\mu$ (nitrate).

The pentaerythritol triazido mononitrate and the pentaerythritol diazido dinitrate can have utility per se as energetic plasticizers, while the alcohols pentaerythritol triazide and pentaerythritol diazido mononitrate have utility as precursors for the preparation of energetic esters, as disclosed and claimed in above copending application Ser. No. 766,459. Thus, as disclosed in such application, both of such alcohols react readily with 4,4,4-trinitrobutyryl chloride to form the polyazido/polynitro substituted esters tris (2,2,2-azidomethyl) ethyl and 3-nitrato-2,2-bis(azidomethyl) propyl 4,4,4-trinitrobutyrates, respectively. The reaction for producing the first mentioned ester is set forth below:

$(NO_2)_3CCH_2CH_2COCl + HOCH_2C(CH_2N_3)_3 \rightarrow$
$(NO_2)_3CCH_2CH_2CO_2CH_2C(CH_2N_3)_3$ A specific example for production of the ester formed in the above noted reaction is as follows:

EXAMPLE VI tris(2,2,2-azidomethyl) ethyl 4,4,4-Trinitrobutyrate

A solution of 3.81 g (0.016 m) of 4,4,4-trinitrobutyryl chloride, 3.06 g (0.014 m) of pentaerythritol triazide, and 10 ml of ethylene dichloride was refluxed for 70 hours. At this time, G.C. analysis showed no starting materials. The reaction mixture was diluted with 20 ml of methylene chloride and stirred with 20 ml of dilute sodium bicarbonate solution for one hour at ambient temperature.

The organic phase was separated, washed with water, dried over magnesium sulfate, passed through a column of neutral alumina, and concentrated to give 5.36 g (91.9%) of yellow oil, $n^{21}D$ 1.5194. The infrared spectrum was consistent for the expected structure of the ester product, with strong absorption at 4.8μ ($N_3$), 5.8μ (C=O), and 6.35μ ($NO_2$). Liquid chromatography (LC) analysis showed only a single component.

From the foregoing, it is seen that the invention provides a facile method for producing diazido and triazido derivatives of pentaerythritol in relatively pure state and which have utility as or in the production of energetic plasticizers for use in formulating solid propellants.

It is to be understood that what has been described is merely illustrative of the principles of the invention and that numerous arrangements in accordance with this invention may be devised by one skilled in the art without departing from the spirit and scope thereof.

What is claimed is:

1. An azido derivative of pentearythritol having the general structural formula:

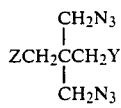

wherein Y is selected from the group consisting of halogen, $ONO_2$ and $N_3$, and Z is selected from the group consisting of OH and $ONO_2$.

2. The compound of claim 1, wherein Y is halogen and Z is OH.

3. The compound of claim 2, wherein Y is Br.

4. The compound of claim 1, wherein Y is $ONO_2$ and Z is OH.

5. The compound of claim 1, wherein Y is $N_3$ and Z is OH.

6. The compound of claim 1, wherein Y is $N_3$ and Z is $ONO_2$.

7. The compound of claim 1, wherein Y is $ONO_2$ and Z is $ONO_2$.

8. A process for producing an azido derivative of pentaerythritol having the structural formula:

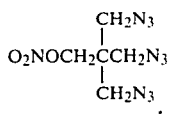

comprising the sequential steps of:

(1) reacting 3,3-bis(azidomethyl)oxetane with a mixture of hydrobromic acid and methylene chloride to produce pentaerythritol diazido monobromide;

(2) reacting the product of step (1) with sodium azide and dimethylsulfoxide to produce pentaerythritol triazide;

(3) further reacting the pentaerythritol triazide of step (2) with a solution of acetic anhydride, methylene chloride and nitric acid; and (4) recovering the reaction product of step (3), pentaerythritol triazido mononitrate, having the structural formula shown above.

9. A process for producing an azido derivative of pentaerythritol having the structural formula:

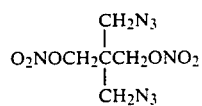

comprising the sequential steps of:

(1) reacting 3,3-bis(azidomethyl)oxetane in methylene chloride with nitric acid to product pentaerythritol diazido monoitrate;

(2) reacting the product of step (1) with a mixture of acetic anhydride, methylene chloride, and nitric acid; and (3) recovering the reaction product of step (2), pentaerythritol diazido dinitrate, having the structural formula shown above.

* * * * *